United States Patent
Dinman

(10) Patent No.: US 9,206,466 B2
(45) Date of Patent: Dec. 8, 2015

(54) COMPOSITIONS AND METHODS FOR REGULATING PEPTIDYLTRANSFERASE ACTIVITY AND USES THEREOF

(75) Inventor: Jonathan D. Dinman, Potomac, MD (US)

(73) Assignee: University of Maryland, College Park, MD (US)

( * ) Notice: Subject to any disclaimer, the term of this patent is extended or adjusted under 35 U.S.C. 154(b) by 2481 days.

(21) Appl. No.: 11/854,273

(22) Filed: Sep. 12, 2007

(65) Prior Publication Data

US 2008/0119387 A1      May 22, 2008

Related U.S. Application Data

(63) Continuation of application No. 10/864,079, filed on Jun. 9, 2004, now abandoned.

(51) Int. Cl.
*C12Q 1/48* (2006.01)
*C12N 9/10* (2006.01)
*C12Q 1/18* (2006.01)

(52) U.S. Cl.
CPC .. *C12Q 1/48* (2013.01); *C12Q 1/18* (2013.01); *G01N 2500/02* (2013.01)

(58) Field of Classification Search
None
See application file for complete search history.

*Primary Examiner* — Maria Marvich
(74) *Attorney, Agent, or Firm* — Darlene A. Vanstone, Esq.; Carolyn S. Elmore, Esq.; Elmore Patent Law Group, P.C.

(57) ABSTRACT

The present invention provides compositions and means to identify compositions that increase −1 PRF programmed ribosomal frameshift (−1PRF) efficiencies and/or decrease peptidyltransferase activity in a cell, and thus directly affect viral replication or assembly of viral particles. Compositions identified in accordance with the invention specifically inhibit the interaction between ribosomal protein L41 and the ribosomes thereby resulting in decreased peptidyltransferase activity of the ribosomes. Decreases in peptidyltransferase activity have been associated with increased −1 PRF efficiencies, which in turn interfere with self assembly of −1PRF dependent viruses thereby interfering with virus propagation. Compositions in accordance with the invention are useful as antiviral therapeutics for treating a viral infection in a patient.

6 Claims, 4 Drawing Sheets

SEQUENCE LISTING

```
<160> NUMBER OF SEQ ID NOS: 18

<210> SEQ ID NO 1
<211> LENGTH: 64
<212> TYPE: DNA
<213> ORGANISM: Artificial Sequence
<220> FEATURE:
<223> OTHER INFORMATION: Synthetic Primer

<400> SEQUENCE: 1
gttcaagaat tgctcgataa ttgcgaacaa accatctgct aagccggaag tcataacaca     60
gtcc                                                                  64

<210> SEQ ID NO 2
<211> LENGTH: 69
<212> TYPE: DNA
<213> ORGANISM: Artificial Sequence
<220> FEATURE:
<223> OTHER INFORMATION: Synthetic Primer

<400> SEQUENCE: 2
ggacgggttt acatgtttaa atatatgtac atgtatgtag tcttataccg tatagaatga     60
tacattacc                                                             69

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
gaaatgtgca aaccttag                                                   18

<210> SEQ ID NO 4
```

```
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
ggaaatagca aaccagag                                                        18

<210> SEQ ID NO 5
<211> LENGTH: 30
<212> TYPE: DNA
<213> ORGANISM: Artificial Sequence
<220> FEATURE:
<223> OTHER INFORMATION: Synthetic Primer

<400> SEQUENCE: 5
ccccggtacc tcatgtacac tggaatgaat                                           30

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer

<400> SEQUENCE: 6
ccccaagctt tgtagtaact gtgttgttc                                            29

<210> SEQ ID NO 7
<211> LENGTH: 29
<212> TYPE: DNA
<213> ORGANISM: Artificial Sequence
<220> FEATURE:
<223> OTHER INFORMATION: Synthetic Primer

<400> SEQUENCE: 7
ccccgaattc aatcatgtct cacagaaag                                            29

<210> SEQ ID NO 8
<211> LENGTH: 32
<212> TYPE: DNA
<213> ORGANISM: Artificial Sequence
<220> FEATURE:
<223> OTHER INFORMATION: Synthetic Primer

<400> SEQUENCE: 8
ccccggatcc ccttacaagt ccttcttcaa ag                                        32

<210> SEQ ID NO 9
<211> LENGTH: 35
<212> TYPE: DNA
<213> ORGANISM: Artificial Sequence
<220> FEATURE:
<223> OTHER INFORMATION: Synthetic Primer

<400> SEQUENCE: 9
ccccgcggcc gcgaagtttt gttagaaaat aaatc                                     35

<210> SEQ ID NO 10
<211> LENGTH: 30
<212> TYPE: DNA
<213> ORGANISM: Artificial Sequence
<220> FEATURE:
<223> OTHER INFORMATION: Synthetic Primer

<400> SEQUENCE: 10
```

-continued

```
ccccgagctc ggacgggttt acatgtttaa                                    30
```

<210> SEQ ID NO 11
<211> LENGTH: 34
<212> TYPE: DNA
<213> ORGANISM: Artificial Sequence
<220> FEATURE:
<223> OTHER INFORMATION: Synthetic Primer

<400> SEQUENCE: 11

```
gcttgtattg gtgcttgcca tccagcccac gttg                               34
```

<210> SEQ ID NO 12
<211> LENGTH: 34
<212> TYPE: DNA
<213> ORGANISM: Artificial Sequence
<220> FEATURE:
<223> OTHER INFORMATION: Synthetic Primer

<400> SEQUENCE: 12

```
gtattggtgc ttggcattca gcccacgttg cttg                               34
```

<210> SEQ ID NO 13
<211> LENGTH: 43
<212> TYPE: PRT
<213> ORGANISM: Homo Sapiens

<400> SEQUENCE: 13

Leu Arg Lys Val Ala Cys Ile Gly Ala Trp His Pro Ala Arg Val Ala
 1               5                  10                  15

Phe Ser Val Ala Arg Ala Gly Gln Lys Gly Tyr His His Arg Thr Glu
                20                  25                  30

Ile Asn Lys Lys Ile Tyr Lys Ile Gly Gln Gly
            35                  40

<210> SEQ ID NO 14
<211> LENGTH: 43
<212> TYPE: PRT
<213> ORGANISM: Drosophila melanogaster

<400> SEQUENCE: 14

Leu Arg Lys Val Ala Cys Ile Gly Ala Trp His Pro Ser Arg Val Ser
 1               5                  10                  15

Thr Thr Val Ala Arg Ala Gly Gln Lys Gly Tyr His His Arg Thr Glu
                20                  25                  30

Ile Asn Lys Lys Ile Tyr Arg Ile Gly Ala Gly
            35                  40

<210> SEQ ID NO 15
<211> LENGTH: 43
<212> TYPE: PRT
<213> ORGANISM: Saccharomyces cerevisiae

<400> SEQUENCE: 15

Leu Arg Lys Val Ala Cys Ile Gly Ala Trp His Pro Ala His Val Met
 1               5                  10                  15

Trp Ser Val Ala Arg Ala Gly Gln Arg Gly Tyr His Ser Arg Thr Ser
                20                  25                  30

Ile Asn His Lys Ile Tyr Arg Val Gly Lys Gly
            35                  40

```
<210> SEQ ID NO 16
<211> LENGTH: 43
<212> TYPE: PRT
<213> ORGANISM: Haloarcula marismortui

<400> SEQUENCE: 16

Arg Arg Arg Ile Gly Asn Leu Gly Pro Trp Asn Pro Ser Arg Val Arg
 1               5                  10                  15

Ser Thr Val Pro Gln Gln Gly Gln Thr Gly Tyr His Gln Arg Thr Glu
            20                  25                  30

Leu Asn Lys Arg Leu Ile Asp Ile Gly Glu Gly
        35                  40

<210> SEQ ID NO 17
<211> LENGTH: 44
<212> TYPE: PRT
<213> ORGANISM: Escherichia coli

<400> SEQUENCE: 17

His Arg Val Pro Gly Ser Ile Gly Gln Asn Gln Thr Pro Gly Lys Val
 1               5                  10                  15

Phe Lys Gly Lys Lys Met Ala Gly Gln Met Gly Asn Glu Arg Val Thr
            20                  25                  30

Val Gln Ser Leu Asp Val Val Arg Val Asp Ala Glu
        35                  40

<210> SEQ ID NO 18
<211> LENGTH: 44
<212> TYPE: PRT
<213> ORGANISM: Thermus thermophilus

<400> SEQUENCE: 18

His Arg His Pro Gly Ser Ile Gly Asn Arg Lys Thr Pro Gly Arg Val
 1               5                  10                  15

Tyr Lys Gly Lys Lys Met Ala Gly His Tyr Gly Ala Glu Arg Val Thr
            20                  25                  30

Val Met Asn Leu Glu Val Val Asp Val Ile Pro Glu
        35                  40
```

COMPOSITIONS AND METHODS FOR REGULATING PEPTIDYLTRANSFERASE ACTIVITY AND USES THEREOF

RELATED APPLICATION

This application is a continuation of U.S. application Ser. No. 10/864,079, filed Jun. 9, 2004. The entire teaching of the above application is incorporated herein by reference.

GOVERNMENT SUPPORT

The invention was supported, in whole or in part, by a grant from the NIH (R01 GM58859) and from the NSF (MCB-9807890). The Government has certain rights in the invention.

BACKGROUND OF THE INVENTION

Programmed ribosomal frameshift (PRF) events most commonly induce translating ribosomes to slip by a single base in either the 5' (−1) or 3' (+1) direction, though examples of ribosomal "hops", "shunts", and "bypasses" have also been documented (reviewed in Jacks, 1990; Farabaugh, 1996; Gesteland & Atkins, 1996). Such translational recoding signals have been valuable in addressing questions relating to ribosome structure and function. For viruses that utilize PRF, the efficiencies of frameshift events are critical: they determine the stoichiometry of viral structural to enzymatic proteins available for virus particle assembly, and altering PRF frequencies have dire consequences for virus propagation (reviewed in Dinman et al., 1998). Thus, it is important to understand how frameshifting efficiencies are controlled. The most widespread mechanisms involve inducing ribosomes to stall with their associated tRNAs positioned over specific mRNA sequences called "slippery sites" such that, in the event of slippage, the tRNAs are able to base pair with the out-of-frame codon or codons. Though the cis-acting signals are relatively well characterized, the trans-acting factors and the biophysical parameters that contribute to determine PRF efficiencies are less well understood. Genetic, biochemical, molecular, and pharmacological methods have been employed toward this end. In general, parameters that can affect PRF efficiencies include: 1) changes in the residence time of ribosomes at a particular PRF signal and the precise steps of the elongation cycle that such kinetic changes might occur; 2) changes in the stabilities of ribosome-bound tRNAs and/or ribosome catalytic function due to alterations in intrinsic ribosomal components such as ribosomal proteins, rRNAs, and codon:antidcodon interactions; and 3) defects in the abilities of the translational apparatus to recognize and correct errors (reviewed in Harger et al., 2002).

The genetic manipulability of the yeast Saccharomyces cerevisiae has facilitated the identification of trans-acting factors that can affect frameshifting efficiencies, and researchers in the field have capitalized on the presence of two endogenous viruses of yeast to this end. The Ty1 retrotransposable element of yeast utilizes a programmed +1 frameshift to synthesize its Gag-pol precursor (Clare et al., 1988; Belcourt & Farabaugh, 1990), and changes in +1 PRF efficiencies have inhibitory effects on Ty1 retrotransposition frequencies (Xu & Boeke, 1990; Kawakami et al., 1993; Balasundaram et al., 1994; Tumer et al., 1998; Harger et al., 2001; Hudak et al., 2001). The 4.6 kb dsRNA L-A virus of yeast utilizes a programmed −1 ribosomal frameshift to produce its Gag-pol fusion protein (Icho & Wickner, 1989; Dinman et al., 1991; Tzeng et al., 1992), and changes in −1 PRF efficiencies promote loss of the killer phenotype as a consequence of loss of the 1.6-1.8 kb dsRNA $M_1$ satellite virus that encodes the secreted killer toxin (reviewed in Wickner, 1996). It has been previously reported that −1 PRF efficiencies were specifically elevated in cells harboring the mak8-1 allele of RPL3 (Peltz et al., 1999), thus providing an explanation for the original observation that mak8-1 cells could not maintain the killer phenotype (Wickner & Leibowitz, 1974; Wickner et al., 1982). Two alleles of RPL3 have been heretofore described: the tcm1-1 allele contains a single missense mutation changing tryptophan at position 255 to cystine (Fried & Warner, 1981), and the mak8-1 allele contains this mutation plus a second missense mutation changing proline at position 257 to threonine. In Example 1 herein, the effects of single and double mutations at this site on −1 PRF, killer virus maintenance, and peptidyltransferase activities in isogenic rpl3 gene deletion strains, are described. A PCR-based mutagenesis approach is employed to identify and characterize a new allele of RPL3 consisting of mutation of isoleucine 282 to threonine (I282T) that was unable to maintain the yeast killer virus. All of the mak8 alleles promoted increased −1 PRF efficiencies, and ribosomes isolated from cells expressing these alleles had decreased peptidyltransferase activities Molecular modeling based on the *Haolarcula marismortui* 50S ribosomal subunit (Ban et al., 2000) reveals that W255 is the closest amino acid residue in the ribosome to the peptidyltransferase center active site, that P257 is required to form an important bend in a loop that positions W255, and that I282 is in the hydrophobic core at the base of the loop. How these structural changes might specifically affect peptidyltransferase function and −1 PRF is discussed within the context of the recent explosion of information pertaining to ribosome structure and function. Further, based on a recent study showing that deletion of ribosomal protein L41 results in peptidyltransferase defects, both −1 and +1 PRF in isogenic rpl41-deficient and wild-type strains were assayed as described herein (see, Example 1). The finding that −1 PRF was also specifically stimulated in rpl41-deficient strains provides additional evidence that −1PRF efficiencies can be influenced by peptidyltransfer rates.

SUMMARY OF THE INVENTION

The present invention provides compositions and methods to identify compositions that increase −1PRF efficiencies, and thus directly affect viral replication or assembly of viral particles. Compositions in accordance with the invention specifically inhibit the interaction between ribosomal protein L41 and the ribosomes thereby resulting in decreased peptidyltransferase activity of the ribosomes. While not intending to be limited to any one scientific theory, it is believed that decreases in peptidyltransferase activity result in increased −1 PRF efficiencies which in turn interfere with self assembly of −1PRF dependent viruses thereby interfering with virus propagation.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
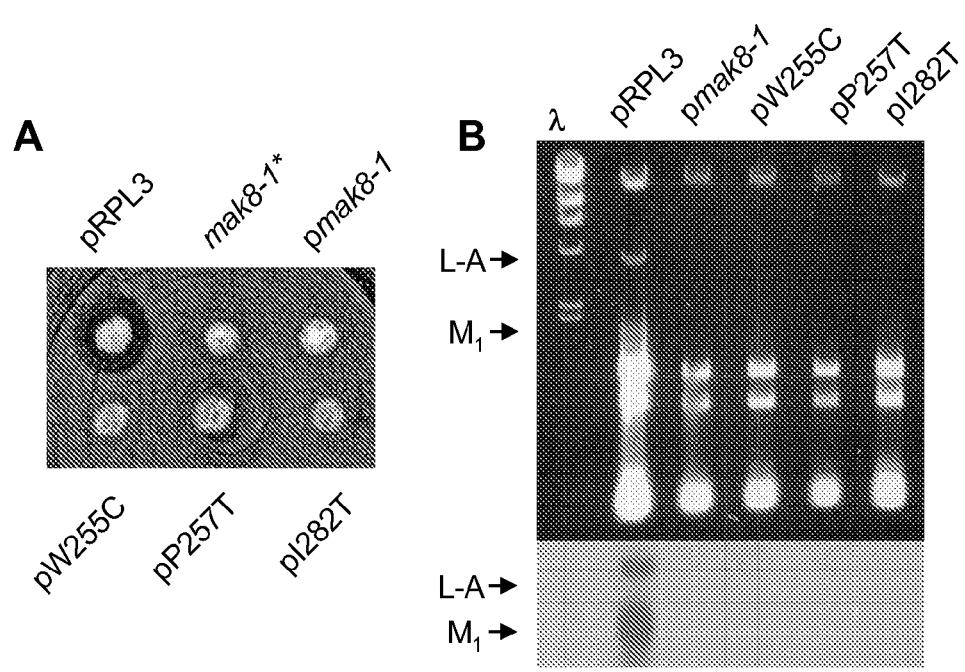
FIGS. 1A and 1B. The rpl3 mutant alleles cannot propagate the yeast killer virus. A. Killer assay of strains harboring the wild-type RPL3 gene or mutant alleles. Isogenic Killer[+] strains containing the RPL3::HIS3 gene disruption and harboring the wild-type RPL3 gene on a URA3-CEN6 plasmid were transformed with TRP1-CEN6 plasmids containing either the wild-type gene or the indicated rpl3 alleles. After selection on medium lacking tryptophan, cells having lost the URA3-CEN6 plasmids were identified by their ability to grow on medium containing 5-FOA. Colonies were then replica plated onto a lawn of cells that are sensitive to the secreted killer toxin produced by the $M_1$ satellite virus of L-A. Killer activity was observed as a zone of growth inhibition around the colonies. mak8-1* is not isogenic with the other strains, but is rather the original mak8-1 isolate (RW1906) used here for comparison. B. Total RNAs isolated from the isogenic strains described in (A) were separated through a 1.5% TAE-agarose gel. L-A and $M_1$ dsRNAs are indicated as 2.5 and 1.8 kbp bands respectively. Top panel shows the ethidium bromide stained gel and the bottom panel is a Northern blot of the gel probed for the presence of L-A and $M_1$ (−) strand viral RNAs were performed as previously described (Dinman & Wickner, 1994).

In a first aspect, the invention provides methods to identify compositions that inhibit peptidyltransferase activity by inhibiting the interaction of L41 with ribosomes, comprising the steps of:
   a) contacting a test composition with a cell or cell extract containing L41 and ribosomes in an amount sufficient to inhibit peptidyltransferase activity;
   b) detecting whether the test composition inhibits the interaction of L41 with the ribosomes; and
   c) determining whether the test composition inhibits peptidyltransferase activity of the ribosomes.

In one non-limiting example of the first aspect of the invention, a cell-based assay system can be devised, in which recombinant ribosomes that have been modified to include a Streptavidin affinity tag in the 25S ribosomal RNA (rRNA) are expressed in a host cell lacking wild-type L41. Also expressed in the same host cell is a recombinant form of L41 that comprises an affinity tag that can bind to a fluorescently labeled indicator molecule. A test composition is introduced into the host cell for a time sufficient to allow the test compound to interact with the tagged L41 protein, and perhaps bind the protein and prevent it from associating with the ribosomes. The cells are then lysed and the contents contacted with streptavidin beads to which the ribosomes will adhere. The beads are then probed with a fluorescent indicator molecule that corresponds to the affinity tag on the L41 protein. Under normal circumstances, L41 should associate with the ribosomes. However, if the test composition displaces L41 from the ribosome or prevents L41 from interacting with the ribosome, unassociated L41 protein remain part of the supernatant and be will be removed when the beads are washed. Fluorescence detected in the wash corresponds to the tagged L41 that was unable to associate with the ribosomes. Peptidyltransferase activity of the ribosomes can then be tested by eluting the ribosomes from the straptavidin beads (e.g. by the addition of biotin) and assaying for peptidyltransferase activity using for example, the puromycin reaction described in Example 1.

Two non-limiting examples of the first aspect of the invention using mechanism-based assays can also be designed around the tagged ribosomes and L41 proteins. In one form, a test composition is introduced into a reaction mixture composed of affinity tagged ribosomes containing the tagged L41 protein for a time sufficient to allow the test compound to interact with the tagged L41 protein, and dissociate the protein from the ribosomes. In another form, test composition is first introduced into a reaction mixture of affinity tagged ribosomes lacking the L41 protein, and after a sufficient time, recombinant tagged L41 is added. In yet another form, the test composition is first introduced into a reaction mixture of affinity tagged ribosomes lacking the L41 protein, and after a sufficient time, recombinant tagged L41 is added: here the compound would inhibit the ability of L41 to initially associate with the ribosome. In both cases, the compound of interest would interfere with the ability of L41 to interact with the ribosome. The reaction mixtures are then contacted with streptavidin beads to which the ribosomes will adhere. The beads are then probed with a fluorescent indicator molecule that corresponds to the affinity tag on the L41 protein. Under normal circumstances, L41 should associate with the ribosomes. However, if the test composition displaces L41 from the ribosome or prevents L41 from interacting with the ribosome, unassociated L41 protein remain part of the supernatant and be will be removed when the beads are washed. Fluorescence detected in the wash corresponds to the tagged L41 that was unable to associate with the ribosomes. Peptidyltransferase activity of the ribosomes can then be tested by eluting the ribosomes from the straptavidin beads (e.g. by the addition of biotin) and assaying for peptidyltransferase activity for example, the puromycin reaction described in Example 1.

As used herein, the term "inhibiting peptidyltransferase" refers to a reduction or decrease in the level of activity of peptidyltransferase of a ribosome as compared to its normal level of peptidyltransferase activity. As used herein the term "inhibiting the interaction of L41 with ribosomes" refers to any alterations in the normal binding and/or interaction between L41 with the ribosomes such as preventing L41 from associating with the ribosome in the normal manner, or displacing L41 from the ribosome, or otherwise altering or preventing the ribosome to carry out its normal activities if L41 was otherwise normally associated with the ribosome. Any composition can be used as a test composition in practicing the invention; preferred test compositions include but are not limited to, polypeptides and small molecules. Although sequence or structural homology can provide a basis for suspecting that a test composition can modulate the interaction with L41 in a cell, randomly chosen test compositions also are suitable for use in the invention. Art-known methods for randomly generating test compositions (e.g., expression of polypeptides from nucleic acid libraries; combinatorial chemistry techniques for generating small molecule chemical libraries) can be used to produce suitable test agent or compositions. Those skilled in the art will recognize alternative techniques can be used in lieu of the particular techniques described herein.

In one embodiment the cell or cell extract may be a yeast cell, cell extract, or purified components such as those from *Saccharomyces cerevisiae*.

In accordance with the present invention such as for the assays described herein, there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

In a second aspect, the invention provides methods of determining whether a test composition increases −1PRF efficiencies of ribosomes by inhibiting the interaction of L41 with the ribosomes, comprising the steps of:
 a) contacting a test composition with a cell or cell extract or purified components mixture containing L41 and ribosomes;
 b) detecting whether the test composition inhibits the interaction of L41 with the ribosomes; and
 c) determining whether −1PRF efficiencies of the ribosomes are increased.

In this second aspect of the invention, the cell may preferably be that of yeast such as *Saccharomyces cerevisiae*. The detecting step may be carried out, for example, using the fluorescence assay described above for identifying whether or not L41 remains associated with the ribosome in the presence of the test composition. The determining step may be carried out using any number of assays for programmed ribosomal frameshifting available in the art including the assay described in Example 1 herein.

In a third aspect of the invention, a method is provided for interfering with virus propagation comprising contacting a cell infected with a virus with an effective amount of a composition identified in accordance with the methods of the invention, that increases −1PRF frameshifting or decreases peptidyltransferase activity.

In a fourth aspect, the invention provides methods for identifying a composition that inhibits binding of L41 to ribosomes comprising the steps of:
 a) contacting a test composition with a cell, cell extract or purified components comprising L41 and ribosomes under conditions sufficient to permit the test compound to interact with L41; and
 b) detecting the presence or absence of binding of L41 to the ribosomes.

In a fifth aspect, the invention provides a composition which inhibits the interaction of L41 with ribosomes and thereby decreases peptidyltransferase activity.

In a sixth aspect, the invention provides a composition which inhibits the interaction of L41 with ribosomes and thereby increases −1PRF.

In a seventh aspect, the invention provides a composition which inhibits interaction of L41 with ribosomes and thereby interferes with self assembly of −1PRF dependent viruses and virus propagation.

In an eighth aspect, the invention provides a method of modulating peptidyl transferase activity comprising contacting a cell with a composition in an amount effective to inhibit the interaction of L41 with the ribosome, thereby modulating peptidyl transferase activity. In a preferred embodiment, peptidyl transferase activity is modulated by being decreased.

In a ninth aspect, the invention provides a method for treating a viral infection in a patient comprising administering to the patient a therapeutically effective amount of a pharmaceutical composition which inhibits the interaction of L41 with ribosomes.

In a tenth aspect, the invention provides a composition which inhibits the interaction of L41 with ribosomes.

In one preferred embodiment of the fifth through tenth aspects of the invention, the composition is a small molecule. In other preferred embodiments, the composition may be a protein, peptide, enzyme, antibody, nucleic acid molecule, gene, antisense molecule, or other molecule that downregulates, inhibits, or interferes with the interaction of L41 with the ribosomes.

The compositions of the invention are useful, for example, in antiviral therapies, particularly against viruses that use the basic −1PRF mechanism, which includes four large families of animal viruses and three large families of plant viruses. For example, almost all retroviruses use −1 ribosomal frameshifting, including lentiviruses (immunodeficiency viruses) such as HIV-1 and HIV-2, SIV, FIV, BIV, Visna virus, Arthritis-encephalitis virus, and equine infectious anemia virus; spumaviruses (the foamy viruses), such as human foamy virus and other mammalian foamy viruses; the T cell lymphotrophic viruses, such as HTLV-I, HTLV-II, STLVs, and BLV; avian leukosis viruses, such as leukemia and sarcoma viruses of many birds, including commercial poultry; type B retroviruses, including mouse mammary tumor virus; and type D retroviruses, such as Mason-Pfizer monkey virus and ovine pulmonary adenocarcinoma virus. In addition, many coronaviruses use the −1 frameshifting, including human coronaviruses, such as the SARS-Associated Coronavirus, 229-E, OC43; animal coronaviruses, such as calf coronavirus, transmissible gastroenteritis virus of swine, hemagglutinating encephalomyelitis virus of swine, and porcine epidemic diarrhea virus; canine coronavirus; feline infectious peritonitis virus and feline enteric coronavirus; infectious bronchitis virus of fowl and turkey bluecomb virus; mouse hepatitis virus, rat coronavirus, and rabbit coronavirus. Similarly, torovirus (a type of coronavirus) is implicated, such as human toroviruses associated with enteric and respiratory diseases; breda virus of calves and bovine respiratory virus; berne virus of horses; porcine torovirus; feline torovirus. Another coronavirus is the arterivirus, which includes simian hemorrhagic fever virus, equine arteritis virus, Lelystad virus (swine), VR2332 virus (swine), and lactate dehydrogenase-elevating virus (rodents). Other animal viruses are paramyxoviruses, such as human −1 ribosomal frameshifting reported in measles, and astroviruses, such as human astroviruses 1-5, and bovine, ovine, porcine, canine, and duck astroviruses.

The plant viruses that involve a −1 frameshifting mechanism include tetraviruses, such as sobemoviruses (e.g., southern bean mosaic virus, cocksfoot mettle virus), leuteoviruses (e.g., barley yellowswarf virus, beet western yellows virus, and potato leaf roll virus), enamoviruses (e.g., pea mosaic virus), and umbraviruses (e.g., carrot mottle virus); tombusviruses, such as tombusvirus (e.g., tomato bushy stunt virus), carmovirus (e.g., carnation mottle virus), necrovirus (e.g., tobacco necrosis virus); dianthoviruses (e.g., red clover necrotic mosaic virus), and machiomovirus (e.g., maize chlorotic mottle virus).

In addition, totiviruses, such as L-A and L-BC (yeast) and other fungal viruses, giradia lamblia virus (intestinal parasite), triconella vaginell virus (human parasite), leishmania brasiliensis virus (human parasite), and other protozoan viruses are −1 frameshift viruses.

The compositions and methods of the present invention are particularly suited to treatment of any animal, particularly a mammal, and more specifically human. Animals to be treated include but are not limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

As used herein, "pharmaceutical composition" comprises a composition in accordance with the invention and a pharmaceutically acceptable carrier. Pharmaceutically acceptable carriers are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

Pharmaceutical compositions in accordance with the invention may be introduced or administered parenterally, transmucosally, transdermally, intramuscularly, intravenously, intradermally, subcutaneously, intraperitonealy, intraventricularly, intracranialy, orally or by inhalation.

The term "therapeutically effective amount" as used herein means an amount of a composition of the invention that is effective, at dosages and for periods of time necessary, to prevent, diminish, inhibit or eradicate symptoms of disease, particularly viral infection, in a patient. A therapeutically effective amount of composition of the invention may vary according to factors such as the disease state, age, sex and weight of the individual. Dosage regimes may be adjusted to provide the optimum therapeutic response. For example, several divided doses may be administered daily or the dose may be proportionally reduced as indicated by the exigencies of the therapeutic situation.

As is appreciated by those skilled in the art the amount of the compound may vary depending on its specific activity and suitable dosage amounts may range from about 0.1 to 20, preferably about 0.5 to about 10, and more preferably one to several, milligrams of active ingredient per kilogram body weight of individual per day and depend on the route of administration. In one embodiment the amount is in the range of 10 picograms per kg to 20 milligrams per kg. In another embodiment the amount is 10 picograms per kg to 2 milligrams per kg. In another embodiment the amount is 2-80 micrograms per kilogram. In another embodiment the amount is 5-20 micrograms per kg. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In yet another embodiment, the therapeutic compound can be delivered in a controlled release system. For example, the complex may be administered using intravenous infusion, an implantable osmotic pump, a transdermal patch, liposomes, or other modes of administration.

The invention will now be described by the following non-limiting examples.

EXAMPLES

Example 1

Summary: Decreased peptidyltransferase activity correlates with increased programmed −1 ribosomal frameshifting and viral maintenance defects in the yeast *Saccharamyces cerevisiae*.

Materials and Methods

Strains, plasmids, genetic manipulation, and media. *E. coli* DH5α, was used to amplify plasmid DNA. Transformation of yeast and *E. coli* were performed as described previously (Cui et al., 1995). YPAD, YPG, SD, synthetic complete medium (H-) and 4.7 MB plates for testing the killer phenotype were as previously reported (Dinman & Wickner, 1994). Restriction enzymes were obtained from Promega, MBI Fermentas, BRL and Boehringer Mannheim. T4 DNA ligase and T4 DNA polymerase were obtained from Boehringer Mannheim and BioRAD, and precision Taq polymerase was obtained from Stratagene. Radioactive nucleotides were obtained from NEN. T7 Sequenase was obtained from USB and Sequagel-6 was obtained from National Diagnostics. DNA sequence analysis was performed by the UMDNJ-RWJMS DNA core facility. Oligonucleotide primers were purchased from IDT. RW1906 (MATa leu2 mak8-1 K$^-$) was a generous gift from Dr. Reed Wickner. PLY36 (MATα rpb1-1 his4-519 ura3-52 trp1-Δ1 upf1Δ::hisG) was a generous gift from Dr. Stuart Peltz. Strain XY5a (MATa ade2-1 trp1-1 his3-11,15 can1-100 ura3-1 leu2-3,112 rpl41a::HIS3 rpl41b::URA3) and pRS314-RPL41A were generous gifts from Dr. Jonathan Warner. The rpl3-knockout (rpl3Δ) strain JD1090 (MATα ura3-52 lys2-801 trp1δ leu2$^=$ his3$^=$ RPL3::HIS3 [L-AHNB M$_1$]) was constructed as follows. The HIS3 gene was first prepared by amplifying it from pRS313 (Sikorski & Hieter, 1989) with primers 5′ HISRPL3 and 3′ HISRPL3 (Table 1).

TABLE 1

Oligonucleotides used in this study.

| Primer name | Sequence |
|---|---|
| 5′HISRPL3 | 5′ GTTCAAGAATTGCTCGATAATTGCGAACAAACCAT CTGCTAAGCCGGAAGTCATAACACAGTCC 3′ SEQ ID NO: 1 |
| 3′HISRPL3 | 5′ GGACGGGTTTACATGTTTAAATATATGTACATGTA TGTAGTCTTATACCGTATAGAATGATACATTACC 3′ SEQ ID NO: 2 |

TABLE 1-continued

Oligonucleotides used in this study.

| Primer name | Sequence |
|---|---|
| RPL3FOR | 5′ GAAATGTGCAAACCTTAG 3′ SEQ ID NO: 3 |
| RPL3REV | 5′ GGAAATAGCAAACCAGAG 3′ SEQ ID NO: 4 |
| 5′UASRPL3 | 5′ CCCCGGTACCTCATGTACACTGGAATGAAT 3′ SEQ ID NO: 5 |
| 3′UASRPL3 | 5′ CCCCAAGCTTTGTAGTAACTGTGTTGTTC 3′ SEQ ID NO: 6 |
| 5′RPL3ORF | 5′ CCCCGAATTCAATCATGTCTCACAGAAAG 3′ SEQ ID NO: 7 |
| 3′RPL3ORF | 5′ CCCCGGATCCCCTTACAAGTCCTTCTTCAAAG 3′ SEQ ID NO: 8 |
| 5′RPL3UTR | 5′ CCCCGCGGCCGCGAAGTTTTGTTAGAAA ATAAATC 3′ SEQ ID NO: 9 |
| 3′RPL3UTR | 5′ CCCCGAGCTCGGACGGGTTTACATGTTTAA 3′ SEQ ID NO: 10 |
| W255C | 5′ GCTTGTATTGGTGCTTGCCATCCAGCCCACG TTG 3′ SEQ ID NO: 11 |
| P257T | 5′ GTATTGGTGCTTGGCATTCAGCCCACGTTGC TTG 3′ SEQ ID NO: 12 |

The resulting PCR fragment harboring ends homologous to sequences flanking the RPL3 gene was integrated into the RPL3 locus in the parental strain (JD111: MATα ura3-52 lys2-801 trp1δ leu2$^=$ his3$^=$ [L-AHNB M$_1$]), harboring pRPL3-URA3. Disruption of the RPL3 locus on the chromosome in His$^+$ prototrophs was confirmed by 1) the inability of cells to grow in the presence of 5-FOA, 2) polymerase chain reaction using primers RPL3FOR and RPL3REV, and 3) Southern blot analysis. Oligonucleotide site directed mutagenesis (Kunkel, 1985) was used to create pRPL3-TRP1 based plasmids harboring the W255C and P257T alleles using the synthetic DNA oligonucleotides W255C and P257T (Table 1). Plasmids for expression of dual luciferase frameshift reporters were constructed by amplification of the coding region of the dual luciferase reporter cassette with the intact polylinker from p2Luci (Grentzmann et al., 1998) by high fidelity PCR and ligation of the product into p416 ADH (Mumberg et al., 1995). In this URA3 CEN6/ARSH4 plasmid, transcription of the dual-luciferase gene is driven by the ADH1 promoter and proper 3′ end formation and polyadenylation is facilitated by the CYC1 terminator. Construction of the L-A −1 and Ty1+1 containing programmed frameshift dual-luciferase reporter plasmids were effected in a similar manner except that the frameshift signals from L-A and Ty1 were first amplified by PCR and subcloned into p2Luci before subsequent amplification and subcloning into p416 ADH. The full details of the construction of these plasmids are described in an accompanying manuscript (Harger and Dinman, submitted).

Preparation and Screening of a Library of Rpl3 Mutants.

To create a library of plasmid-borne rpl3 mutants, a strategy was devised so that DNA fragments harboring the coding region of RPL3 amplified by standard error-prone PCR mutagenesis methods (Costa & Weiner, 1995) could be ligated into a pRS314 (TRP1)-based plasmid 3' of the native RPL3 promoter, and 5' of the RPL3 3' UTR. To make the parental plasmid construct, the RPL3 5' UTR was amplified from genomic DNA using the 5' UASRPL3 and 3' UASRPL3 primers (Table 1). This was then cloned into pRS314 digested with Kpn I and Hind III. Subsequently, the RPL3 open reading frame was amplified from genomic DNA using the 5' RPL3ORF and 3' RPL3ORF primers (Table 1) and cloned into the Eco RI and Bam HI sites downstream of the 5' UTR. The 3' UTR the RPL3 gene was then amplified using the 5' RPL3 UTR and 3' RPL3 UTR primers (Table 1), and the PCR product was cloned into the Not I and Sac I sites downstream of the RPL3 ORF. Digestion of the resulting plasmid (pRPL3-TRP1) with Eco RI and Bam HI was used to liberate it from the native RPL3 coding region, into which a library of PCR fragments were ligated. Due to the relatively large size of the RPL3 coding sequence, standard Taq polymerase was used to generate the PCR fragments. DNA sequence analysis confirmed that 19 of 20 randomly selected plasmids each contained 1 unique mutation per RPL3 coding region. The library was amplified in *E. coli*, introduced into JD1090 yeast cells by transformation, and after three days growth on selective medium (-trp) cells that had lost the wild-type RPL3 containing plasmids were identified by replica plating on 5-flourorotic acid (5-FOA) (Rose et al., 1990). Colonies were replica plated onto killer indicator plates to identify those that had lost the killer virus phenotype. Plasmids were rescued from Killer⁻ cells into *E. coli*, and re-introduced into JD1090 cells. Only those that were able to completely cure the cells of the killer phenotype were selected as new mak8 alleles. Approximately $3 \times 10^4$ colonies were screened.

Assays for the Killer Phenotypes, Measurement of Frameshifting, and mRNA Analyses.

The killer virus assay was carried out as previously described (Dinman & Wickner, 1992). Briefly, yeast colonies were replica plated to 4.7 MB plates newly seeded with 0.5 $O.D._{595}$ of the killer indicator strain 5x47 (MATa/MATα his1/+trp1/+ura3/+K⁻) per plate. After 2-3 days at 20° C., killer activity was observed as a zone of growth inhibition around the killer colonies. Killer virus assays were performed in multiple wild-type and mutant strains. Assays of programmed ribosomal frameshifting using monocistronic lacZ reporter constructs were performed as previously described (Dinman et al., 1991; Peltz et al., 1998) using LEU2-CEN6 based series of 0-frame control (p0), and −1 PRF (p−1) frameshift indicator vectors, or URA3-CEN6 based series of 0-frame control (p0) and Ty1-derived +1 PRF (p+1) frameshift indicator vectors. Mid-logarithmically growing yeast cells were harvested, the optical density of the sample at 595 nm ($O.D._{595}$) readings were recorded, and cells were pelleted by centrifugation. Cells were resuspended in 500 ml of Z-buffer+2-mercaptoethanol (100 mM $PO_4$ pH7.0, 10 mM KCl, 1 mM $MgSO_4$, 0.1 mM 2-mercaptoethanol. SDS (100 μl of a 0.1% solution) and chloroform (100 μl) were added to permeablize the cells, and the reaction mixture was pre-incubated for 10 min. at 28° C. Orthonitrophenyl galactoside (ONPG) was then added (100 μl of a 4 mg/ml aqueous solution), the reactions were allowed to proceed for a set amount of time, after which they were stopped by addition of 250 μl of 1 M $Na_2CO_3$. Cell debris was pelleted by centrifugation, and optical densities of the reactions were determined at 420 nm ($O.D._{420}$). Beta-galactosidase (β-gal) activities were calculated by the following formula:

$$\beta\text{-gal} = (1/O.D._{595}) \times (1 \text{ hr}) \times (O.D._{420}).$$

Percent frameshifting was calculated by dividing the β-gal activities of the frameshift test samples (p−1) by those of the zero frame control (p0) and multiplying by 100%.

All assays were performed three times in triplicate to determine mean and standard deviations of frameshifting efficiencies. To monitor programmed −1 and +1 frameshifting using the dual luciferase reporter plasmids, glass beads were used to prepare lysates from cells expressing the 0-frame, −1 (L-A derived), or +1 (Ty1 derived) dual-luciferase plasmids. After clarification of the lysates by centrifugation, typically 5 μl were used in a total volume of 100 μl of Dual-Luciferase Assay Reagents (Promega), and the *Renilla* and firefly luciferase activities were quantitiated using a TD20/20 luminometer (Turner designs). Frameshifting efficiencies were calculated by dividing the firefly/*Renilla luminescence* ratios from lysates of cells expressing the −1 or +1 programmed frameshift test reporters by the same ratio obtained from lysates of cells expressing the 0-frame control reporter. All assays were performed three separate times each in triplicate. Extraction of total nucleic acids (TNA) and RNA-RNA hybridizations to detect the presence of L-A and $M_1$ (−) strand RNAs were performed as previously described (Dinman & Wickner, 1994). Briefly, to extract TNA, cells were pelleted from an overnight liquid culture in an eppendorf tube, supernates were removed, and cell pellets resuspended and washed in 0.5 ml of 50 mM EDTA. Cells were again pelleted, supernates removed, resuspended in 0.5 ml 50 mM Tris $SO_4$ pH 9.3+2.5% β-ME and allowed to stand for 15 min. at room temperature. Cells were again pelleted by centrifugation, supernates removed, and resuspended in 400 μl of a solution containing 0.1 M NaCl, 10 mM Tris Cl pH 7.5, 10 mM EDTA, and 0.2%. An equal volume of phenol was added, and samples were allowed to mix gently on a platform rocker for 1 hr at room temperature. The aqueous and organic layers were separated by centrifugation, the aqueous phase extracted once more with phenol/chloroform, and total nucleic acids were precipitated from the aqueous layer with 1 ml 100% ethanol, 40 μl of 3M NaOAc. For RNA-RNA hybridizations, 10 mg of TNA were separated through 1.2% native agarose gels, dsRNA was separated in the gel into ssRNA using a 50% formamide/9.25% formaldehyde solution, and the nucleic acids were transferred to nitrocellulose or nylon membranes. L-A (−) strand probe was made by T3 RNA polymerase run off transcripts of EcoRV digested pLM1 (Fujimura and Wickner, 1992). $M_1$ (−) strand probes were made by T3 RNA polymerase run off transcripts of PstI-digested p596, which contains the 1.3 kb PstI-SalI fragment from an $M_1$ cDNA inserted into the BlueScript KS+ vector. Membranes were pre-hybridized for 6 hr at 55° C. in 50% formamide, 5×SSC, 50 mM Na HPO4, pH 6.8., 0.1% SDS, 1 mM EDTA, and 0.05% each BSA, Ficoll, and polyvinylpyrrolidone, and then hybridized in the same buffer overnight at 55° C. Membranes were washed in five changes of 0.1S SSC, 0.1% SDS at 65° C. for 20 min and exposed for autoradiography. The abundance of mature CYH2 and CYH2-precursor mRNAs were determined by Northern blot analysis as previously described (Cui et al., 1996). Nuclease protection assays were performed to monitor reporter mRNA abundances as previously described probing for the LacZ mRNAs generated from the p0 and p−1 plasmids (Harger et al, 2001). Briefly, RNA (10 μg) from each sample was resuspended to a total volume of 21 μl in hybridization buffer (40 mM PIPES pH 6.4, 1 mM EDTA, 0.4 M NaCl, 80% formamide). The buffer contained excess probe. A 200 nt [$\alpha^{32}$P]CTP labelled lacZ (−) strand probe generated from a T7 RNA polymerase runoff transcript of Hinc II digested pJD86 (Dinman and Wickner, 1994). The CYH2 gene encodes the constitutively expressed ribosomal protein L29 and was used as loading control. Hybridization initially occurred at 70° C. for 15 min, and then at 50° C. for 5 hrs. RNase T1 and RNase A (200 µl of a 300 mM NaCl, 10 mM Tris pH 7.5, 5 mM EDTA buffer containing 286 U of T1 and 0.72 µg of RNase A) were added to the annealed RNAs and incubated at room temperature for 15 min. Seventeen µl of a proteinase K/SDS solution (1:4 ratio of proteinase K 10 mg/ml/10% SDS) was added and reactions were incubated for 15 min at 37° C. The reactions were extracted with an equal volume of phenol/chloroform equilibrated to pH7.5, centrifuged for 5 min, the aqueous layers taken, carrier tRNA (20 µg) was added, and nucleic acids were precipitated with 2.5 volumes of ethanol at −20° C. for 15 min. Dried pellets were resuspended in 20 µl of loading dye, denatured at 100° C. for 3 min, and RNA samples were electrophoretically separated through 6% polyacrylamide denaturing gels which were dried and exposed to autoradiography. The protected RNA fragments were quantitated by using a Bio-Rad model G-670 imaging densitometer. The relative lacZ mRNA abundances were calculated by determining the ratio of lacZ to CYH2 protected RNA fragment band intensities.

Preparation of Donor and Acceptor tRNA Fragments, Ribosome Purification and Puromycin Reaction with Purified Fragments.

Yeast tRNAs were charged with [$^{14}$C]Phenylalanine using a preparation of yeast tRNA synthetases purified by DEAE-cellulose treatment of yeast lysates as previously described (Wurmbach & Nierhaus, 1979). Charged tRNAs were acetylated essentially as previously described (Haenni & Chapeville, 1966) by resuspending [$^{14}$C]Phe-tRNA$^{Phe}$ in 280 µl of 1.0 M sodium acetate (pH 5.5) followed by addition of 28 µl aliquots of acetic anhydride every 15 min for a total of one hour at 0° C. These reaction products were precipitated and washed with ethanol, resuspended in water and 100% of the [$^{14}$C]Phe-tRNA$^{Phe}$ was determined to acetylated as judged by TLC chromatography. The acetyl-[$^{14}$C]Phe-tRNA$^{Phe}$ was subsequently digested with 500 U of RNase T1 in 200 µl of 0.3 M sodium acetate (pH 5.0) for 1 hour at 37EC, and the reaction mixtures were purified using DEAE Sephadex as previously described (Pestka et al., 1970). The resulting acetyl-[$^{14}$C]Phe-CACCA was used as the "donor" fragment in the puromycin assay. 80S ribosomes were prepared from wild type and mutant strains as described (Triana et al., 1994) with minor modifications. Briefly, cells were grown to early mid-log phase, spun down and washed with Buffer A [5 mM Mg(CH$_3$COO)$_2$, 20 mM Tris-HCl pH 7.5 at +4° C., 50 mM KCl, 10% Glycerol]. Cells (6-20 g) were suspended in 25 ml of Buffer A and PMSF and DTE were added to final concentrations of 1 mM each. Cells were disrupted with Bead-Beater (Biospec Inc) at 4° C. Cell lysates were transferred to centrifuge tubes and spun 10 min at 4000 rpm in a Sorvall SS34 rotor. A 4M stock solution of KCl was added to the supernatants to a final concentration of 0.5M, and then centrifuged in an SS34 rotor for 45 min at 15,000 rpm. Supernatants were transferred to Beckman 14×89 mm (13 ml) tubes containing 3 ml of Buffer B [5 mM Mg(CH$_3$COO)$_2$, 20 mM Tris-HCl pH 7.5 at 30° C., 0.5 M KCl, 10% Glycerol] and ribosomes were pelleted at 24,000 rpm for 18-24 hours. Ribosomes were treated with puromycin to strip endogenous peptidyl-tRNA, mRNA, and soluble factors from ribosomes. Pellets were washed to remove the fines by gentle mixing with Buffer B and ribosomes were resuspended in 1 ml of Buffer B containing 1 mM PMSF and DTE. Puromycin and GTP, both at 1 mM final concentrations were added and the mix was incubated for 30 min at 30° C. Ribosomes were washed by pelleting twice through a 25% Glycerol cushion in the same buffer. The washed ribosomes were resuspended in Buffer C [50 mM Tris-HCl pH 7.5, 5 mM Mg(CH$_3$COO)$_2$, 50 mM NH$_4$Cl, 0.1 mM PMSF, 0.1 mM DTE, 25% Glycerol], clarified by centrifugation for 5 min at 4000 rpm, and ribosome concentrations were adjusted to 5-10 pmol/µl (1 A$_{260}$ unit=20 pmol of 80S subunits). Ribosomes were either immediately used or aliquotted and stored at −80° C. Puromycin reactions were performed as previously described (Diedrich et al., 2000) with slight modifications. Ribosomes (20 pmol) were incubated with 5 pmol of acetyl-CACCA[$^{14}$C]Phe (682 d.p.m./pmol) in 300 µl of PR Buffer [25 mM HEPES-KOH pH 7.4, 135 mM NH$_4$Cl, 250 mM KCl, 20 mM MgCl$_2$, 33% EtOH] at 0° C. for 10 min. Puromycin was added to final concentrations of 1 mM, and reaction mixes were incubated on ice. At indicated time points 50 µl aliquots were taken and reactions stopped by the addition of equal volumes of a 0.3 M NaOAc solution saturated with MgSO$_4$. Peptidyl-puromycin was extracted with 1 ml of EtOAc and the radioactivity was determined by liquid scintillation counting. In all the studies controls were performed in the absence of puromycin to determine the nonspecific extraction of CACCA[$^{14}$C]AcPhe. Control values (generally less than 2%) were subtracted from the values obtained in the presence of puromycin. All assays were performed in triplicate.

Computational Analysis of Ribosome Structure.

The crystal structure of the *Haloarcula marismortui* ribosome (Ban et al., 2000) was visualized using the Swiss PDB viewer.

Results

Identification of New Mak8 Alleles.

The original mak8-1 allele contained two mutations: W255C and P257T (Peltz et al., 1999), and cells expressing this form of the L3 protein had increased −1 PRF efficiencies and were not able to maintain the killer virus. Toward the goal of further analyses of RPL3, we set out to 1) determine the effects of the single mutations, and 2) to identify additional mak8 alleles. The single mutations were constructed by oligonucleotide site directed mutagenesis, and additional alleles were created using error-prone PCR. The PCR fragments were ligated into a TRP1-CEN6 vector containing the native 5' and 3' untranslated region sequences of RPL3, and the resulting plasmids were amplified in *E. coli*. The library, and the site-directed mutants were introduced into a Killer$^+$ rpl3-deletion yeast strain (rpl3Δ), in which the native RPL3 gene was expressed from a URA3-CEN6 vector (pRPL3). After three days of growth on medium lacking tryptophan (-trp), colonies were replica-plated to medium containing 5-FOA, allowing for selection of loss of the wild-type RPL3 gene. Subsequent replica plating to 4.7 MB killer indicator plates enabled identification of mak8 alleles of RPL3 by loss of the Killer phenotype. After screening over 30,000 colonies, only one novel mutant was identified: a missense mutation that changed isoleucine at position 282 to threonine (I282T). Also identified in the screen were single mutants encoding the W255C and P257T alleles. Approximately 10% of the mutants were lethal (data not shown), though dominant-lethal mutants would not be identified by the methods employed. Sequence analysis of 20 randomly chosen clones from the library revealed 19 different unique mutants at the nucleotide level, suggesting that the library was mutagenized to saturation. The killer phenotypes of these and of the original RW1906 mak8-1 strain are shown in FIG. 1A. FIG. 1B shows that loss of the killer phenotype in all of these strains was a consequence of the inability of these cells to support propagation of both the L-A and M$_1$ satellite viruses as opposed to a defect in the synthesis or secretion of the M$_1$ encoded killer toxin. The differences between the abilities of the L3 mutants expressed in the new rpl3Δ strains and the original mak8-1 strain to maintain L-A may be due to differences in their genetic backgrounds and/or a consequence of episomal expression of RPL3. Thus, in addition to the original mak8-1 allele the single missense mutants (W255C and P257T), as well as I282T appear to be the only viable alleles of RPL3 that are unable to maintain both the L-A and M$_1$ dsRNA viruses.

The Rpl3 Alleles Specifically Promote Increased Efficiencies of Programmed −1 Ribosomal Frameshifting.

Figure 2:
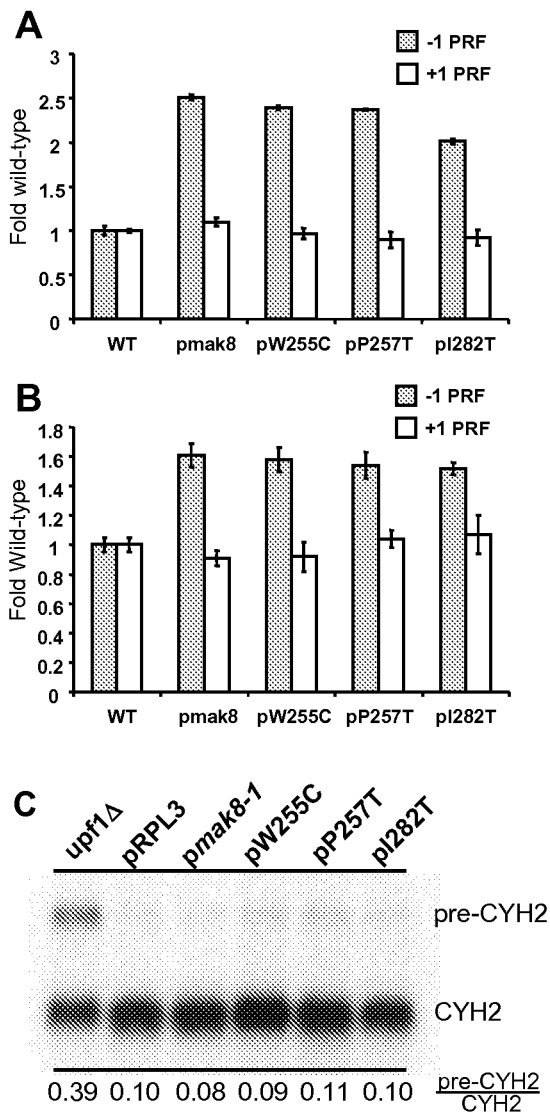
FIGS. 2A, 2B and 2C. Elevated efficiencies of −1 programmed ribosomal frameshifting in cells expressing mutant rpl3. A. Monscistronic PRF reporter plasmid system. Isogenic strains harboring the TRP1-CEN6 based RPL3 alleles were co-transformed with p0 or p−1 (LEU2-CEN6 based vectors), or p0 or p+1 (URA3-CEN6) and programmed ribosomal frameshifting efficiencies were determined as described (Dinman et al., 1991; Peltz et al., 1999). Changes in frameshift efficiencies are depicted in terms of fold wild-type (see Table 2). Each dataset represents the averages of three individual experiments repeated in triplicate. Error bars denote standard deviations from the means. B. Bicistronic PRF reporter plasmid system. Isogenic strains harboring the TRP1-CEN6 based RPL3 alleles were co-transformed with bicistronic URA3-CEN6 based Renilla-firefly luciferase 0-frame, −1 (L-A derived), or +1 (Ty1-derived) reporter vectors. Renilla and firefly luciferase activities of clarified cell lysates were determined using Dual-Luciferase Assay Reagents (Promega) and quantitated using a TD20/20 lumineter (Turner designs). Frameshifting efficiencies were calculated by dividing the firefly/Renilla luminescence ratios from the −1 and +1 programmed frameshift test reporters by the 0-frame control reporter. Each dataset represents the averages of three individual experiments repeated in triplicate. Changes in frameshift efficiencies are depicted in terms of fold wild-type (see Table 2). Error bars denote standard deviations from the means. C. Expression of mutant forms of L3 do not affect the nonsense mediated mRNA decay (NMD) pathway. Total cellular mRNA was extracted from mid-logarithmically growing rpl3Δ cells harboring plasmids encoding the wild-type or mutant alleles of RPL3 as indicated. mRNA from PLY36 cells harboring the upf1Δ::hisG allele (upf1Δ) was used as a control. Total RNA from each sample was separated through a 1.0% agarose formaldehyde denaturing gel and transferred to a nylon membrane. The RNA blot was subsequently hybridized with a radiolabeled CYH2 probe as previously described (Cui et al., 1996). The image was visualized, and band intensities were quantitated using a Molecular Dyanmics phosphorimager. The locations of the NMD-sensitive CYH2-precursor mRNA (pre-CYH2) and of the NMD-insensitive mature CYH2 mRNA are indicated, as are the pre-CYH2/CYH2 signal intensity ratios.

M$_1$ satellite virus propagation defects can stem from other causes distinct from changes in −1 PRF efficiency, e.g. ribosomal 60S subunit biogenesis defects (Dinman & Wickner, 1994; Ohtake & Wickner, 1995). Measurements of programmed ribosomal frameshifting in the mutants using our traditional monocistronic lacZ reporter plasmid system revealed that they all promoted approximately 2-2.5 fold increases in −1 PRF efficiencies as promoted by an L-A −1 frameshift signal but that none of these alleles had any effect on Ty1 mediated +1 PRF (FIG. 2A, Table 2).

The monocistronic −1 and +1 frameshift reporter LacZ mRNAs can be considered to be nonsense-containing mRNAs, and increased translational efficiency of a nonsense-containing mRNA has been demonstrated to result as a consequence of defects in the nonsense-mediated mRNA decay (NMD) pathway (Muhlrad & Parker, 1999). Thus, it is possible that our observations could have been due to similar defects, although if so, we would have expected to observe similar effects of the mutants on both −1 and +1 PRF instead of on −1 PRF alone. Two additional sets of experiments were performed in order to formally address this possibility.

Bicistronic reporter systems have been used in yeast to control for effects due to variations in mRNA stabilities, half-lives, or translation rates that might differentially affect reporter gene expression from monocistronic reporter systems (Bidou et al, 2000). To this end, we utilized a series of plasmids for the expression of bicistronic dual-luciferase frameshift reporters in yeast. In agreement with data obtained using the lacZ-based monocistronic reporters, the bicistronic system revealed that programmed −1 ribosomal frameshifting was also elevated in cells expressing the mutant forms of L3 as compared to cells expressing the wild-type Rpl3 protein and that Ty1 directed +1 frameshifting was not affected (FIG. 2B, Table 2). Comparison of the results obtained using the mono- and bicistronic reveals two interesting differences: 1) baseline −1 PRF efficiencies were greater with the bicistronic system, and 2) the extents of the increases in −1 PRF in the mutants were smaller (e.g. 1.4-1.7 fold as opposed to 2.0-2.5 fold increases). We speculate that the former may be consequent to elimination of effects due differential stabilities and/or translational efficiencies of the frameshift reporter and 0-frame control mRNAs. The latter observation could either be due to inherent differences between the systems, or may simply reflect a more accurate picture of the true changes in −1 PRF. If true, then the acceptable "window" of −1 PRF sufficient for virus propagation is considerably smaller than was previously thought. Regardless of the differences in magnitude of the changes in −1 PRF using the different reporter systems, the results demonstrate that the inabilities of cells harboring the different rpl3 alleles to maintain the L-A and M$_1$ viruses are a consequence of increased efficiencies of −1 PRF.

A second set of experiments examined whether expression of the L3 mutants had specific effects on LacZ reporter mRNA steady state abundances, and/or non-specific effects on the ability of the translational apparatus to recognize and degrade aberrant mRNAs. To address the question of mRNA specificity, RNase protection studies demonstrated that there were no significant differences in the −1 or +1 frameshift to 0-frame LacZ control steady-state mRNA abundance in the mutants as compared to the wild-type control cells, suggesting that the observed changes are specific to −1 PRF and are not due to specific stabilization of the −1 frame reporter message (data not shown). To directly address the question of NMD defects, Northern blot analysis of the endogenous inefficiently spliced CYH2-precursor mRNA was used to monitor the NMD status of cells expressing the wild-type RPL3 and mutant rpl3 alleles. As a control, the abundance of the CYH2-precursor mRNA was also monitored in a upf1-deletion strain. FIG. 2C shows that the rpl3 mutants had no stabilizing effect on CYH2-precursor mRNA, demonstrating that the NMD pathway was intact in these strains, and that the effects on −1 PRF cannot be explained by possible NMD defects.

Ribosomes Containing the Mutant Forms of L3 have Decreased Peptidyltransfer Activities.

Figure 3:
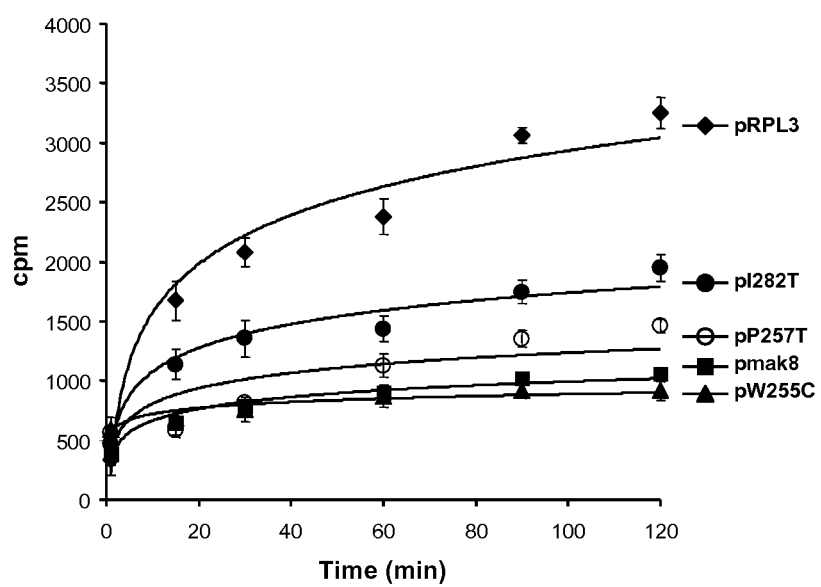
FIG. 3. Ribosomes containing mutant forms of L3 have decreased peptidyltransferase activities. Time course of the formation of [$^{14}$C]Phenylalanine-puromycin product in assays using ribosomes isolated from isogenic RPL3::HIS3 cells expressing wild-type or mutant forms of L3. Plasmid-borne RPL3 alleles are indicated. EtOAc soluble radioactivity was determined by liquid scintillation counting. Control studies were performed in the absence of puromycin to determine the nonspecific extraction of CACCA[$^{14}$C]AcPhe. Control values (generally less than 2%) were subtracted from the values obtained in the presence of puromycin. All experiments were performed in triplicate. Data points and error bars indicate mean and standard deviation.

Ribosomal protein L3 has long been implicated in peptidyltransferase activity (Fahnestock, 1975; Bernabeu et al., 1979; Auron & Fahnestock, 1981; Fabijanski & Pellegrini, 1981; Schulze & Nierhaus, 1982; Khaitovich et al., 1999). Our recent models of programmed ribosomal frameshifting predict that inhibition of the peptidyltransfer reaction would increase the amount of time that a ribosome is paused over the frameshift signal after the accommodation step of elongation, increasing the likelihood of −1 ribosomal frameshifting (Harger et al., 2002; Plant et al., 2003). This prediction was previously indirectly validated by the demonstration that the peptidyltransferase inhibitor sparsomycin promoted increased −1 PRF efficiencies and loss of the killer virus in yeast (Dinman et al., 1997). In this study, we utilized the puromycin reaction to test the hypothesis that the defects in peptidyltransferase activities were responsible for the increased −1 PRF efficiencies in cells harboring the mak8 alleles. The results demonstrate that rates of peptidylpuromycin formation are significantly decreased in ribosomes containing the mutant L3 proteins (FIG. 3). The W255C mutation conferred the greatest peptidyltransfer defect, while the P257T mutation also promoted a strong, but slightly lesser effect. The effects of the two mutations were not additive. The I282T mutation also resulted in a significant, though lesser degree of inhibition of peptidyltransferase activity. These results support the hypothesis that decreased peptidyltransferase activities of the ribosomes containing these mutant forms of L3 constitute the biochemical basis for the observed effects of the rpl3 alleles on −1 PRF and killer virus maintenance.

Programmed −1 Ribosomal Frameshifting is Stimulated in Ribosomal Protein L41 Deficient Cells.

Figure 4:
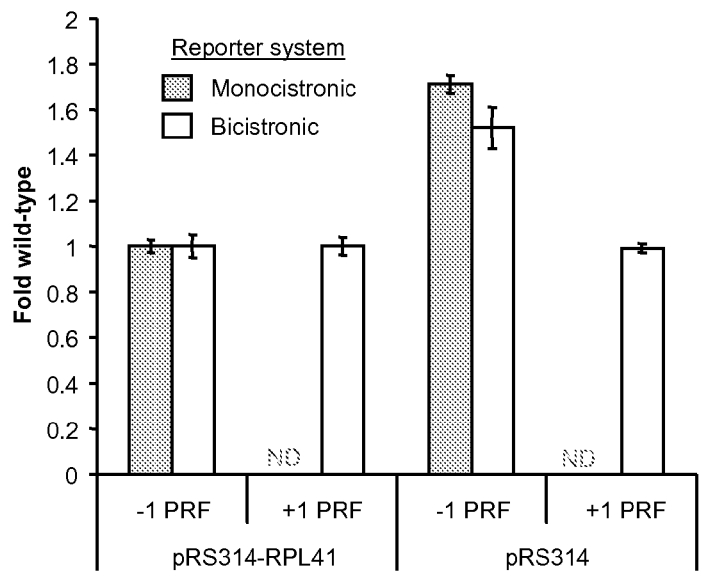
FIG. 4. Programmed −1 ribosomal frameshifting is specifically stimulated in L41-deficient yeast cells. Isogenic XY5a strains (MATa ade2-1 trp1-1 his3-11,15 can1-100 ura3-1 leu2-3,112 rpl41a::HIS3 rpl41b::URA3) harboring pRS314-RPL41A or pRS314 were co-transformed with either monocistronic or bicistronic p0, p−1 or p+1 LEU2-CEN6 based reporter vectors. Changes in frameshift efficiencies are depicted in terms of fold wild-type (see Table 2). Programmed ribosomal frameshifting efficiencies using the monocistronic reporters were determined as described (Dinman et al., 1991; Peltz et al., 1998). ND: not determined. In the assays using the bicistronic reporter system, Renilla and firefly luciferase activities of clarified cell lysates were determined using Dual-Luciferase Assay Reagents (Promega) and quantitiated using a TD20/20 lumineter (Turner designs). Frameshifting efficiencies were calculated by dividing the firefly/Renilla luminescence ratios from the −1 and +1 programmed frameshift test reporters by the 0-frame control reporter. Each dataset represents the averages of three individual experiments repeated in triplicate. Error bars denote standard deviations from the means.

It has recently been demonstrated that ribosomes lacking ribosomal protein L41 have peptidyltransferase defects (Dresios et al, 2003). With a length of only 25 amino acid, 17 of which are arginine or lysine, yeast ribosomal protein L41 is the smallest and most basic eukaryotic protein (Suzuki et al, 1990). Deletion of the two isogenes encoding this protein (RPL41A and RPL41B) did not affect cell viability or NMD (Yu & Warner, 2001; Dresios et al, 2003). As a test of the generality of our hypothesis we assayed both −1 and +1 PRF in the XY5a cells harboring pRS314-RPL41A or the pRS314 vector control (Yu & Warner, 2001) using the dual-luciferase reporter system (Harger and Dinman, 2003). Briefly, cells harboring the pYDL −1 PRF reporter (pYDL-L-A) and 0-frame control (pYDL-control) plasmids were grown in H-uracil liquid media (1 ml) to an O.D.$_{595nm}$ of 0.7. Cells were harvested by centrifugation and washed once with 1 ml of ice cold lysis buffer (1×PBS pH 7.4, 1 mM PMSF) and then resuspended in 0.3 ml of the same buffer. Cells suspensions were lysed with glass beads, cell debris pelleted by centrifugation, and supernates were taken. Typically the concentrations of crude lysates were between 0.1 and 1.0 mg/ml as determined by the Bradford method (BioRad). Luciferase activities were determined using 5 µl of lysate/sample using the Dual-Luciferase™ Assay System (Promega). Frameshift efficiencies were calculated using the previously described method (Grentzmann et al. 1998) using a TD 20/20 luminometer (Turner Designs). The firefly/*Renilla* activity ratio generated from the control reporter (pYDL-control) was divided into that from the frameshift reporter (pYDL-LA) and multiplied by % 100 to obtain frameshift efficiencies for each recoding signal. All assays were performed in triplicate at least 3 times. The results clearly show that −1 PRF was specifically stimulated 1.5-1.7-fold in cells lacking L41 and that the presence or absence of L41 had no effect on +1 PRF (FIG. 4, Table 2). These results support the general existence of a correlation between peptidyltransferase defects and increased efficiencies of −1 PRF.

Discussion

The propagation of many clinically and agriculturally relevant viruses depends upon the availability of precise ratios of viral proteins as determined by the efficiency of PRF. Thus, a better understanding of the molecular mechanisms underlying the control of PRF can contribute toward identifying and characterizing new targets for the rational design of antiviral therapies. There is strong evidence biochemical showing that ribosomal pausing is necessary but not sufficient for efficient −1 PRF (Lopinski et al., 2000; Kontos et al., 2001). We have posited that changes in ribosome pause times at specific steps of the translation elongation cycle would result in changes in both the direction and extent of frameshifting (Harger et al., 2002). Specific to −1 PRF, we have suggested that the mechanism becomes activated at accommodation when 5' movement of the A-site codon:anticodon pair combines with the inability of the 3' mRNA pseudoknot to enter the downstream mRNA tunnel to create a local of region tension along the mRNA between these two elements (Plant et al., 2003). Thus, conditions that would increase the amount of time that ribosomes are paused at the frameshift signal after accommodation but before peptidyltransfer should increase the amount of time during which they might slip. Our previous studies using the peptidyltransferase inhibitor sparsomycin and mutants of RPL3 indirectly supported this hypothesis (Dinman et al., 1997; Peltz et al., 1999). In the present study, we demonstrate that increased −1 PRF and decreased peptidyltransfer correlate. The lack of effect of the new L3 mutants described here, and of the L41-deficient strains on both +1 PRF and NMD demonstrate that the observed effects on −1 PRF and virus maintenance are not due to non-specific effects of altered translational competence of our reporter mRNAs. The results presented here demonstrate a correlation between changes in peptidyltransferase activity and programmed −1 ribosomal frameshifting efficiency. Another recent study from our laboratory demonstrating a correlation between decreased peptidyltransferase activity and increased −1 PRF in mutants of RPD3/MOF6 further supports this theory (Meskauskas et al., 2003), as does an independent study in *E. coli* demonstrating that changes in ribosomal pause times correlated with changes in programmed −1 ribosomal frameshifting (Masucci et al., 2002).

Protein synthesis is the primary function of the ribosome and peptidyltransfer is the most central molecular reaction.

Thus, one question posed by this and another recent study (Dresios et al., 2002) is why significant growth phenotypes are not associated with cells harboring peptidyltransferase-defective ribosomes. An examination of the kinetics of each of the steps of translation elongation suggests the answer. in vitro measurements using *E. coli* derived ribosomes and cofactors reveal that whereas the rates of peptidyltransfer (20 $s^{-1}$) (Southworth et al, 2002) and EF-G catalyzed translocation (18 $s^{-1}$) (Sementov et al, 2000) are similar, the rate limiting steps in elongation are aa-tRNA accommodation (8 $s^{-1}$) and dissociation of EF-Tu.GDP from the ribosome (4 $s^{-1}$) (Pape et al, 1998). Thus, even though these mutant ribosomes exhibit significant peptidyltransferase defects, rates of elongation are likely not significantly affected. However, it is possible that peptidyltransferase function was sufficiently decreased to render this step rate limiting in at least some of the 10% of rpl3 alleles that were found to be lethal in this study.

Figure 5:
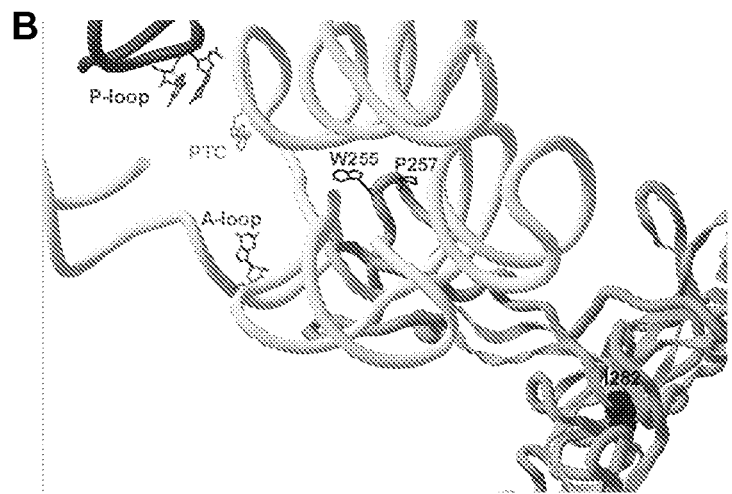
FIGS. 5A and 5B. L3 and the peptidyltransferase center. A. ClustalW alignment of selected regions of ribosomal protein L3. The primary amino acid sequences from six representative species in the vicinity of the amino acids of L3 examined in this study were aligned. L3 sequences were from the following species: H. Sapiens (SEQ ID NO: 13) (HsL3 from amino acids 247-290), D. melanogaster (SEQ ID NO: 14) (DmL3, from amino acids 247-290), S. cerevisiae (SEQ ID NO: 15) (ScL3 from residues 244-287), H. marismortui (SEQ ID NO: 16) (HaL3 from residues 233-276), E. coli (SEQ ID NO: 17) (EcL3 from residues 139-183), and T. thermophilus (SEQ ID NO: 18) (TtL3 from amino acids 134-178). The three amino acids of interest to this study are highlighted. B. Is a map of the L3 mutants within in the context of the H. marismortui 50S crystal structure at 2.4 Å.

Comparison of ribosomes from all three superkingdoms reveals that there has been strong selection for conservation of the fine structure of this complex biomachine (Ban et al., 2000; Wimberly et al., 2000; Mueller et al., 2000; Morgan et al., 2000; Yusupov et al., 2001; Spahn et al., 2001; Harms et al., 2001). Comparison of the crystal structures of the *H. marismortui* 50S subunit at 2.4 Å (Ban et al., 2000), the *T. thermophilus* 70S ribosome at 5.5 Å resolution (Yusupov et al., 2001), the *D. radiodurans* 50S subunit at 3.1 Å (Harms et al., 2001), and the most recent cryo-EM analysis of the yeast 80S ribosome (Spahn et al., 2001) reveals that the overall L3 structure and its placement in the ribosome is highly conserved between all of these organisms. Multiple sequence alignment of L3 protein sequences from 6 representative organisms (*H. sapiens, D. melanogaster, S. cerevisiae, H. Marismortui, E. coli*, and *T. thermophilus*) reveals that the three residues genetically identified in this study are highly conserved (FIG. 5A). The proline (yeast P257) is universal. The tryptophan (yeast W255) is conserved in eukaryotes and archea. Notably, the corresponding glutamine in *E. coli* (Q298) is methylated, and lack of this modification results in a cold-sensitive phenotype (Lhoest & Colson, 1981). We suggest that methylation of this glutamine in *E. coli* reduces its polarity, thus making the local environment more similar to that created by the tryptophan in the eukaryotic and archael systems. The isoleucine (yeast I282) is also conserved in eukaryotes with neutral changes to leucine in *H. marismortui* (L270), and valine in *E. coli* and *T. thermophilus* (V177 and V172 respectively).

FIG. 5B depicts the *H. marismortui* L3 protein in relation to the rRNA environment surrounding the peptidyltransferase center. The tryptophan of L3 corresponding to yeast W255 is at the end of a "finger" that protrudes into the center of the large subunit. This marks the closest approach of any amino acid in the ribosome (~18 Å) to the peptidyltransferase catalytic center (Yellow, *E. coli* A2451; *H. marismortui* 2486; yeast 2876). The observation that the double mutant (W255C+P257T) had no greater effect on either frameshifting or peptidyltransferase activity as compared to W255C alone suggests that this amino acid plays an important role in the formation and activity of the peptidyltransferase center. However, since mutation of the universally conserved proline (yeast P257) also resulted in strong peptidyltransferase inhibition and stimulation of −1 PRF, we suggest that its function may be to form an important bend in the finger so as to correctly position W255. The third residue (yeast I282) is in the hydrophobic core at the base of the finger: though I→T is fairly conservative, we suspect that the addition of a polar hydroxyl side group is sufficient to alter the structure of the core, misaligning the finger. This would account for the observed effects of this mutant on both −1 PRF and peptidyltransferase activity.

L41 presents a particularly attractive target for potential antiviral therapeutics. One could envisage that small molecules able to interfere with or alter interactions between L41 and the ribosome would result in ribosomes having decreased peptidyltransferase activities. This would promote increased −1 PRF efficiencies, which would in turn interfere with self assembly of −1 PRF dependent viruses interfering with virus propagation. Thus, one would predict that such a class of small molecules would have antiviral properties. A number of specific properties of this protein make it a particularly attractive target. It is highly conserved from humans to yeast and its non-essential status in yeast suggests that inhibiting its function would not have a lethal impact on human cellular functions. Its extremely small size is also advantageous for both biophysical and economic reasons. At the physical level, the impact of synthetic small molecules would be expected to be greater on a protein of relatively similar size rather than a significantly larger one. Economically, chemical synthesis of 25 amino acid peptides is very inexpensive, enhancing the cost effectiveness of high throughput screens. The demonstrated reliance on −1 PRF of HIV-1 as well as the presumed reliance of the SARS-associated Coronavirus on this mechanism (Marra et al, 2003; Rota et al., 2003) suggests that the general findings presented here are of more than academic interest.

REFERENCES

Auron P E, Fahnestock S R. 1981. Functional organization of the large ribosomal subunit of *Bacillus stearothermophilus*. *J Biol Chem* 256:10105-10110.

Balasundaram D, Dinman J D, Wickner R B, Tabor C W, Tabor H. 1994. Spermidine deficiency increases +1 ribosomal frameshifting efficiency and inhibits Ty1 retrotransposition in *Saccharomyces cerevisiae*. *Proc Natl Acad Sci USA* 91:172-176.

Ban N, Nissen P, Hansen J, Moore P B, Steitz T A. 2000. The complete atomic structure of the large ribosomal subunit at 2.4 Å resolution. *Science* 289:905-920.

Belcourt M F, Farabaugh P J. 1990. Ribosomal frameshifting in the yeast retrotransposon Ty: tRNAs induce slippage on a 7 nucleotide minimal site. *Cell* 62:339-352.

Bernabeu C, Conde P, Vazquez D, Ballesta J P. 1979. Peptidyl transferase of bacterial ribosome: resistance to proteinase K. *Eur J Biochem* 93:527-533.

Bidou L, Stahl G, Hatin I, Namy O, Rousset J-P, Farabaugh P J. 2000. Nonsense-mediated decay mutants do not affect programmed −1 frameshifting. *RNA* 6: 952-961.

Clare J J, Belcourt M, Farabaugh P J. 1988. Efficient translational frameshifting occurs within a conserved sequence of the overlap between the two genes of a yeast Ty1 transposon. *Proc Natl Acad Sci USA* 85:6816-6820.

Costa G L, Weiner M P. 1995. Cloning and analysis of PCR-generated DNA fragments. In: Dieffenbach C W, Dveksler G S, eds. *PCR primer: a laboratory manual*. Cold Spring Harbor, N.Y.: Cold Spring Harbor Press. pp 555-580.

Cui Y, Dinman J D, and Peltz S W. 1996. mof4-1 is an allele of the UPF1/IFS2 gene which affects both mRNA turnover and −1 ribosomal frameshifting efficiency. *EMBO J* 15: 5726-5736.

Cui Y, Hagan K W, Zhang S, Peltz S W. 1995. Identification and characterization of genes that are required for the accelerated degradation of mRNAs containing a premature translational termination codon. *Genes & Dev* 9:423-436.

Diedrich G, Spahn C M, Stelzl U, Schafer M A, Wooten T, Bochkariov D E, Cooperman B S, Traut R R, Nierhaus K H. 2000. Ribosomal protein L2 is involved in the association of the ribosomal subunits, tRNA binding to A and P sites and peptidyl transfer. *EMBO J* 19:5241-5250.

Dinman J D, Icho T, Wickner R B. 1991. A −1 ribosomal frameshift in a double-stranded RNA virus forms a Gag-pol fusion protein. *Proc Natl Acad Sci USA* 88:174-178.

Dinman J D, Ruiz-Echevarria M J, Czaplinski K, Peltz S W. 1997. Peptidyl transferase inhibitors have antiviral properties by altering programmed −1 ribosomal frameshifting efficiencies: development of model systems. *Proc Natl Acad Sci USA* 94:6606-6611.

Dinman J D, Ruiz-Echevarria M J, Peltz S W. 1998. Translating old drugs into new treatments: Identifying compounds that modulate programmed −1 ribosomal frameshifting and function as potential antiviral agents. *Trends in Biotech* 16:190-196.

Dinman J D, Wickner R B. 1992. Ribosomal frameshifting efficiency and Gag/Gag-pol ratio are critical for yeast $M_1$ double-stranded RNA virus propagation. *J Virology* 66:3669-3676.

Dinman J D, Wickner R B. 1994. Translational maintenance of frame: mutants of *Saccharomyces cerevisiae* with altered −1 ribosomal frameshifting efficiencies. *Genetics* 136:75-86.

Dresios J, Panopoulos P, Suzuki K, and Syntenos D. 2002. A dispensable yeast ribosomal protein optimizes peptidyl-transferase activity and affects translocation. *J. Biol. Chem.* 278: 3314-3322

Fabijanski S, Pellegrini M. 1981. Identification of proteins at the peptidyl-tRNA binding site of rat liver ribosomes. *Mol Gen Genet* 184:551-556.

Fahnestock S R. 1975. Evidence of the involvement of a 50S ribosomal protein in several active sites. *Biochemistry* 14:5321-5327.

Farabaugh P J. 1996. Programmed translational frameshifting. *Microbiol Rev* 60:103-134.

Fried H M, Warner J R. 1981. Cloning of yeast gene for trichodermin resistance and ribosomal protein L3. *Proc Natl Acad Sci USA* 78:238-242.

Fujimura, T and Wickner R B. 1992. Interaction of two cis sites with the RNA replicase of the yeast L-A virus. *J. Biol. Chem.* 267:2708-2713.

Gesteland R F, Atkins J F. 1996. Recoding: Dynamic reprogramming of translation. *Annu Rev Biochem* 65:741-768.

Grentzmann G, Ingram J A, Kelly P J, Gesteland R F, Atkins J F. 1998. A dual-luciferase reporter system for studying recoding signals. *RNA* 4: 479-486.

Haenni A L, Chapeville F. 1966. The behavior of acetylphenylalanyl soluble ribonucleic acid in polyphenylalanine synthesis. *Biochim Biophys Acta* 114:135-148.

Harger, J W and Dinman, J D. 2003. An in vivo dual-luciferase assay system for studying translational recoding in the yeast *Saccharomyces cerevisae*. *RNA* 9:1019-1024.

Harger J W, Meskauskas A, Dinman J D. 2002. An 'integrated model' of programmed ribosomal frameshifting and post-transcriptional surveillance. *TIBS* 27:448-454.

Harger J W, Meskauskas A, Nielsen N, Justice M C, Dinman J D. 2001. Ty1 retrotransposition and programmed +1 ribosomal frameshifting require the integrity of the protein synthetic translocation step. *Virology* 286:216-224.

Harms J, Schluenzen F, Zarivach R, Bashan A, Gat S, Agmon I, Bartels H, Franceschi F, Yonath A. 2001. High resolution structure of the large ribosomal subunit from a mesophilic eubacterium. *Cell* 107:679-688.

Hudak K A, Hammell A B, Yasenchak J, Turner N E, Dinman J D. 2001. A C-terminal deletion mutant of pokeweed antiviral protein inhibits programmed +1 ribosomal frameshifting and ty1 retrotransposition without depurinating the sarcin/ricin loop of rRNA. *Virology* 279:292-301.

Icho T, Wickner R B. 1989. The double-stranded RNA genome of yeast virus L-A encodes its own putative RNA polymerase by fusing two open reading frames. *J Biol Chem* 264:6716-6723.

Jacks T. 1990. Translational suppression in gene expression in retroviruses and retrotransposons. *Curr Top Microbiol Immunol* 157:93-124.

Kawakami K, Paned S, Faioa B, Moore D P, Boeke J D, Farabaugh P J, Strathern J N, Nakamura Y, Garfinkel D J. 1993. A rare tRNA-Arg(CCU) that regulates Ty1 element ribosomal frameshifting is essential for Ty1 retrotransposition in *Saccharomyces cerevisiae*. *Genetics* 135:309-320.

Khaitovich P, Mankin A S, Green R, Lancaster L, Noller H F. 1999. Characterization of functionally active subribosomal particles from Thermus aquaticus. *Proc Natl Acad Sci USA* 96:85-90.

Kontos H, Napthine S, Brierley I. 2001. Ribosomal pausing at a frameshifter RNA pseudoknot is sensitive to reading phase but shows little correlation with frameshift efficiency. *Mol Cell Biol* 21:8657-8670.

Kunkel T. 1985. Rapid and efficient site-specific mutagenesis without phenotype selection. *Proc Natl Acad Sci USA* 82:488-492.

Lhoest J, Colson C. 1981. Cold-sensitive ribosome assembly in an *Escherichia coli* mutant lacking a single methyl group in ribosomal protein L3. *Eur J Biochem* 121:33-37.

Lopinski J D, Dinman J D, Bruenn J A. 2000. Kinetics of Ribosomal Pausing during Programmed −1 Translational Frameshifting. *Mol Cell Biol* 20:1095-1103.

Marra M A, Jones S J, Astell C R, Holt R A, Brooks-Wilson A, Butterfield Y S, Khattra J, Asano J K, Barber S A, Chan S Y, Cloutier A, Coughlin S M, Freeman D, Girn N, Griffith O L, Leach S R, Mayo M, McDonald H, Montgomery S B, Pandoh P K, Petrescu A S, Robertson A G, Schein J E, Siddiqui A, Smailus D E, Stott J M, Yang G S, Plummer F, Andonov A, Artsob H, Bastien N, Bernard K, Booth T F, Bowness D, Drebot M, Fernando L, Flick R, Garbutt M, Gray M, Grolla A, Jones S, Feldmann H, Meyers A, Kabani A, Li Y, Normand S, Stroher U, Tipples G A, Tyler S, Vogrig R, Ward D, Watson B, Brunham R C, Krajden M, Petric M, Skowronski D M, Upton C, Roper R L. 2003. The Genome Sequence of the SARS-Associated Coronavirus. *Science* 300:1399-1404.

Masucci J P, Gallant J, Lindsley D, Atkinson J. 2002. Influence of the relA gene on ribosome frameshifting. *Mol. Genet. Genomics* 268: 81-86.

Meskauskas A, Dinman J D. 2001. Ribosomal protein L5 helps anchor peptidyl-tRNA to the P-site in *Saccharomyces cerevisiae*. *RNA* 7:1084-1096.

Meskauskas A, Baxter J L, Carr E A, Yasenchak J., Gallagher J E G, Baserga S J, Dinman J D. 2003. Delayed rRNA processing results in significant ribosome biogenesis and functional defects. *Mol. Cell. Biol.* 23: 1602-1613.

Morgan D G, Menetret J F, Radermacher M, Neuhof A, Akey I V, Rapoport T A, Akey C W. 2000. A comparison of the yeast and rabbit 80 S ribosome reveals the topology of the nascent chain exit tunnel, inter-subunit bridges and mammalian rRNA expansion segments. *J Mol Biol* 301:301-321.

Mueller F, Sommer I, Baranov P, Matadeen R, Stoldt M, Wohnert J, Gorlach M, van Heel M, Brimacombe R. 2000. The 3D arrangement of the 23 S and 5 S rRNA in the *Escherichia coli* 50 S ribosomal subunit based on a cryo-electron microscopic reconstruction at 7.5 A resolution. *J Mol Biol* 298:35-59.

Muhlrad D, Parker R. 1999. Recognition of yeast mRNAs as "nonsense containing" leads to both inhibition of mRNA translation and mRNA degradation: implications for the control of mRNA decapping. *Mol. Biol. Cell* 11: 3971-3978.

Mumberg D, Muller R, Funk M. 1995. Yeast vectors for the controlled expression of heterologous proteins in different genetic backgrounds. *Gene* 156: 119-122.

Ohtake Y, Wickner R B. 1995. Yeast virus propagation depends critically on free 60S ribosomal subunit concentration. *Mol Cell Biol* 15:2772-2781.

Pape, T, Wintermeyer W, and Rodnina M V. 1998. Complete kinetic mechanism of elongation factor Tu-dependent binding of aminoacyl-tRNA to the A site of the *E. coli* ribosome. *EMBO J* 17: 7490-7497.

Peltz S W, Hammell A B, Cui Y, Yasenchak J, Puljanowski L, Dinman J D. 1999. Ribosomal Protein L3 Mutants Alter Translational Fidelity and Promote Rapid Loss of the Yeast Killer Virus. *Mol Cell Biol* 19:384-391.

Pestka S, Hishizawa T, Lessard J L. 1970. Studies on the formation of transfer ribonucleic acid-ribosome complexes. 8. Aminoacyl oligonucleotide binding to ribosomes: characteristics and requirements. *J Biol Chem* 245: 6208-6219.

Plant E P, Muldoon Jacobs K I, Harger J W, Meskauskas A, Jacobs J L, Baxter J L, Petrov A N, Dinman, J D. 2003. The 9-Å solution: how mRNA pseudoknots promote efficient programmed −1 ribosomal frameshifting. *RNA* 9: 168-174.

Rose M D, Winston F, Hieter P. 1990. *Methods in Yeast Genetics*. Cold Spring Harbor, N.Y.: Cold Spring Harbor Press.

Rota P A, Oberste M S, Monroe S S, Nix Wash., Campagnoli R, Icenogle J P, Penaranda S, Bankamp B, Maher K, Chen M H, Tong S, Tamin A, Lowe L, Frace M, DeRisi J L, Chen Q, Wang D, Erdman D D, Peret T C, Burns C, Ksiazek T G, Rollin P E, Sanchez A, Liffick S, Holloway B, Limor J, McCaustland K, Olsen-Rassmussen M, Fouchier R, Gunther S, Osterhaus A D, Drosten C, Pallansch M A, Anderson L J, Bellini W J. 2003. Characterization of a Novel Coronavirus Associated with Severe Acute Respiratory Syndrome. *Science* 300: 1394-1399. Schulze H, Nierhaus K H. 1982. Minimal set of ribosomal components for reconstitution of the peptidyltransferase activity. *EMBO J* 1:609-613.

Semenkov Y P, Rodnina M V, Wintermeyer W. 2000. Energetic contribution of tRNA hybrid state formation to translocation catalysis of the ribosome. *Nature Struct. Biol* 7: 1027-1031.

Sikorski R S, Hieter P. 1989. A system of shuttle vectors and yeast host strains designed for efficient manipulation of DNA in *Saccharomyces cerevisiae*. *Genetics* 122:19-27.

Southworth D R, Brunelle J L, Green R. 2002. EFG-independent translocation of the mRNA:tRNA complex is promoted by modification of the ribosome with thiol-specific reagents. *J. Mol. Biol.* 324: 611-623.

Spahn C M, Beckmann R, Eswar N, Penczek P A, Sali A, Blobel G, Frank J. 2001. Structure of the 80S ribosome from *Saccharomyces cerevisiae*—tRNA-ribosome and subunit-subunit interactions. *Cell* 107:373-386.

Suzuki K, Hashimoto T, and Otaka E. Yeast ribosomal proteins: XI. Molecular analysis of two genes encoding YL41, an extremely small and basic ribosomal protein, from *Saccharomyces cerevisiae*. *Curr. Genet.* 17: 185-190.

Triana F, Nierhaus K H, Chakraburtty K. 1994. Transfer RNA binding to 80S ribosomes from yeast: evidence for three sites. *Biochem Mol Biol Int* 33:909-915.

Tumer N E, Parikh B, Li P, Dinman J D. 1998. Pokeweed antiviral protein specifically inhibits Ty1 directed +1 ribosomal frameshifting and Ty1 retrotransposition in *Saccharomyces cerevisiae*. *J Virol* 72:1036-1042.

Tzeng T H, Tu C L, Bruenn J A. 1992. Ribosomal frameshifting requires a pseudoknot in the *Saccharomyces cerevisiae* double-stranded RNA virus. *J Virol* 66:999-1006.

Wickner R B. 1996. Double-stranded RNA viruses of *Saccharomyces cerevisiae*. *Microbiol Rev* 60:250-265.

Wickner R B, Leibowitz M J. 1974. Chromosomal and non-chromosomal mutations affecting the "killer character" of *Saccharomyces cerevisiae*. *Genetics* 76:423-432.

Wickner R B, Porter-Ridley S, Fried H M, Ball S G. 1982. Ribosomal protein L3 is involved in replication or maintenance of the killer double-stranded RNA genome of *Saccharomyces cerevisiae*. *Proc Natl Acad Sci USA* 79:4706-4708.

Wimberly B T, Brodersen D E, Clemons W M, Jr., Morgan-Warren R J, Carter A P, Vonrhein C, Hartsch T, Ramakrishnan V. 2000. Structure of the 30S ribosomal subunit. *Nature* 407:327-339.

Wurmbach P, Nierhaus K H. 1979. Isolation of the protein synthesis elongation factors EF-Tu, EF-Ts, and EF-G from *Escherichia coli*. *Methods Enzymol* 60:593-606.

Xu J, Boeke J D. 1990. Host genes that influence transposition in yeast: the abundance of a rare tRNA regulates Ty1 transposition frequency. *Proc Natl Acad Sci USA* 87:8360-8364.

Yu X, and Warner J R. Expression of a micro-protein. 2001. *J. Biol. Chem.* 276: 33821-33825.

Yusupov M M, Yusupova G Z, Baucom A, Lieberman K, Earnest T N, Cate J H, Noller H F. 2001. Crystal Structure of the Ribosome at 5.5 A Resolution. *Science* 292:883-896.

Yusupova G Z, Yusupov M M, Cate J H, Noller H F. 2001. The path of messenger RNA through the ribosome. *Cell* 106:233-241.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a composition which inhibits peptidyl transferase activity by inhibiting the interaction of L41 with ribosomes, comprising the steps of:
   a) contacting a test composition with a cell, a cell extract, or purified cell components containing L41 and ribosomes, wherein the test composition is a small molecule or polypeptide;
   b) detecting whether the test composition specifically inhibits the interaction of L41 with the ribosomes; and
   c) determining whether the test composition inhibits peptidyl transferase activity of the ribosomes.

2. The method of claim 1, wherein the cell or cell extract is from yeast.

3. The method of claim 1, wherein the determining step comprises detecting a decrease in the rate of peptidylpuromycin formation by the ribosomes.

4. A method of identifying a composition which increases −1 programmed ribosomal frameshift (PRF) efficiencies by inhibiting the interaction of L41 with ribosomes comprising the steps of:
   a) contacting a test composition with a cell, a cell extract, or purified cell components, containing L41 and ribosomes, wherein the test compound is a small molecule or polypeptide;
   b) detecting whether the test composition inhibits the interaction of L41 with the ribosomes; and
   c) determining whether the test composition increases −1 programmed ribosomal frameshift (PRF) efficiencies of the ribosomes.

5. The method of claim 4, wherein the cell is a yeast cell.

6. The method of claim 4, wherein the determining step comprises an assay of programmed ribosomal frameshifting.

* * * * *